United States Patent
Clarke

(10) Patent No.: US 10,363,081 B2
(45) Date of Patent: Jul. 30, 2019

(54) APPARATUS, PROBE AND METHOD FOR A CRYOGENIC SYSTEM

(71) Applicant: Nitro Medical Limited, Staffordshire (GB)

(72) Inventor: Brian Clarke, Nottinghamshire (GB)

(73) Assignee: NITRO MEDICAL LIMITED, Staffordshire (GB)

( * ) Notice: Subject to any disclaimer, the term of this patent is extended or adjusted under 35 U.S.C. 154(b) by 576 days.

(21) Appl. No.: 14/439,883

(22) PCT Filed: Oct. 30, 2012

(86) PCT No.: PCT/GB2012/052700
§ 371 (c)(1),
(2) Date: Apr. 30, 2015

(87) PCT Pub. No.: WO2014/068262
PCT Pub. Date: May 8, 2014

(65) Prior Publication Data
US 2015/0297279 A1    Oct. 22, 2015

(51) Int. Cl.
*A61B 18/02* (2006.01)
*A61B 18/00* (2006.01)

(52) U.S. Cl.
CPC .......... *A61B 18/0218* (2013.01); *A61B 18/02* (2013.01); *A61B 2018/00041* (2013.01); *A61B 2018/0212* (2013.01); *A61B 2018/0262* (2013.01); *A61B 2018/0275* (2013.01); *A61B 2018/0281* (2013.01); *A61B 2018/0293* (2013.01)

(58) Field of Classification Search
CPC ................ A61B 18/02; A61B 18/0218; A61B 2018/00041; A61B 2018/0212; A61B 2018/0262; A61B 2018/0293
USPC ....................................................... 606/20–26
See application file for complete search history.

(56) References Cited

U.S. PATENT DOCUMENTS

| | | | | | |
|---|---|---|---|---|---|
| 3,786,814 | A | * | 1/1974 | Armao | A61B 18/02 604/113 |
| 3,911,924 | A | * | 10/1975 | Zimmer | A61B 18/02 606/24 |
| 3,948,269 | A | * | 4/1976 | Zimmer | A61B 18/02 606/24 |

(Continued)

FOREIGN PATENT DOCUMENTS

EP    0 955 012 A1    11/1999
GB    2 005 000 A    4/1979
(Continued)

OTHER PUBLICATIONS

PCT/GB2012/052700—International Search Report, dated Aug. 13, 2013.
(Continued)

*Primary Examiner* — Michael F Peffley
(74) *Attorney, Agent, or Firm* — Curatolo Sidoti Co., LPA; Salvatore A. Sidoti; Floyd Trillis, III

(57) ABSTRACT

An apparatus, probe and method for a cryogenic system are described. According to certain embodiments of the invention there is provided an apparatus for cryosurgery comprising: an exhaust line configured to receive cryogen from a probe; and a vacuum source configured to be in fluid communication with the exhaust line.

21 Claims, 12 Drawing Sheets

(56) References Cited

U.S. PATENT DOCUMENTS

| | | | |
|---|---|---|---|
| 4,022,215 A * | 5/1977 | Benson | A61B 18/02 606/21 |
| 4,345,598 A * | 8/1982 | Zobac | A61B 18/02 606/24 |
| 5,334,181 A | 8/1994 | Rubinsky et al. | |
| 5,520,682 A * | 5/1996 | Baust | A61B 18/02 606/20 |
| 5,674,218 A * | 10/1997 | Rubinsky | A61B 18/02 606/20 |
| 6,306,129 B1 | 10/2001 | Little et al. | |
| 6,355,029 B1 * | 3/2002 | Joye | A61B 18/02 606/21 |
| 6,383,180 B1 * | 5/2002 | Lalonde | A61B 18/02 606/22 |
| 6,565,556 B1 * | 5/2003 | Korpan | A61B 18/02 606/20 |
| 2004/0078033 A1 | 4/2004 | Levin | |
| 2004/0243119 A1 | 12/2004 | Lane et al. | |
| 2005/0010200 A1 * | 1/2005 | Damasco | A61B 18/02 606/21 |
| 2009/0088735 A1 | 4/2009 | Abboud et al. | |
| 2009/0157065 A1 * | 6/2009 | Levin | A61B 18/02 606/23 |
| 2009/0287202 A1 | 11/2009 | Ingle et al. | |
| 2010/0241112 A1 * | 9/2010 | Watson | A61B 18/02 606/21 |
| 2010/0319360 A1 | 12/2010 | Niedbala et al. | |
| 2011/0054453 A1 | 3/2011 | Lalonde | |

FOREIGN PATENT DOCUMENTS

| | | |
|---|---|---|
| GB | 2 336 781 A | 11/1999 |
| GB | 2 336 782 A | 11/1999 |
| GB | 2 337 000 A | 11/1999 |
| JP | 1992-218680 | 7/1992 |
| JP | 1993-168646 | 2/1993 |
| JP | 2009-112563 | 5/2009 |
| WO | WO 92/04872 | 4/1992 |

OTHER PUBLICATIONS

PCT/GB2012/052700—International Written Opinion, dated Aug. 13, 2013.
GB1305137.0—Great Britain Search Report, dated May 1, 2013.
GB1313303.8—Great Britain Search Report, dated Jan. 22, 2014.
GB1313304.6—Great Britain Search Report, dated Jan. 24, 2014.

* cited by examiner

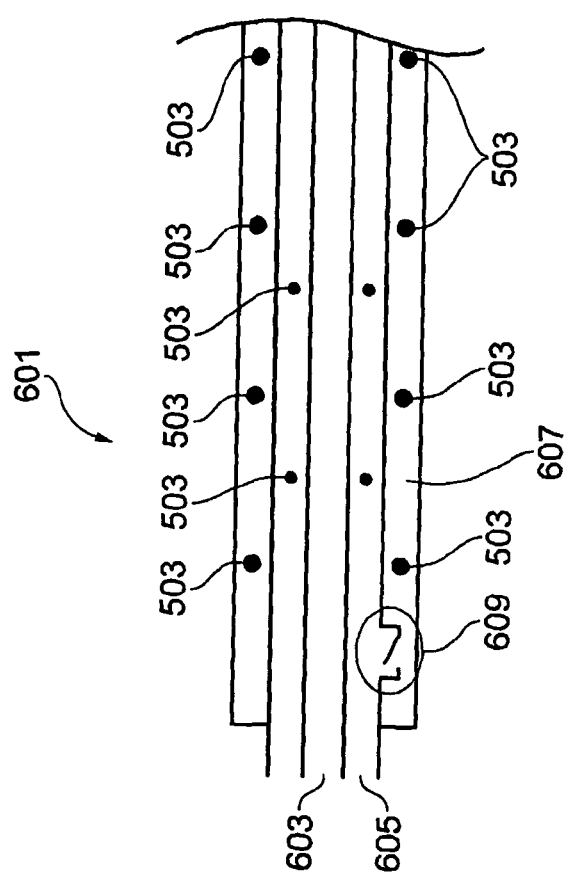

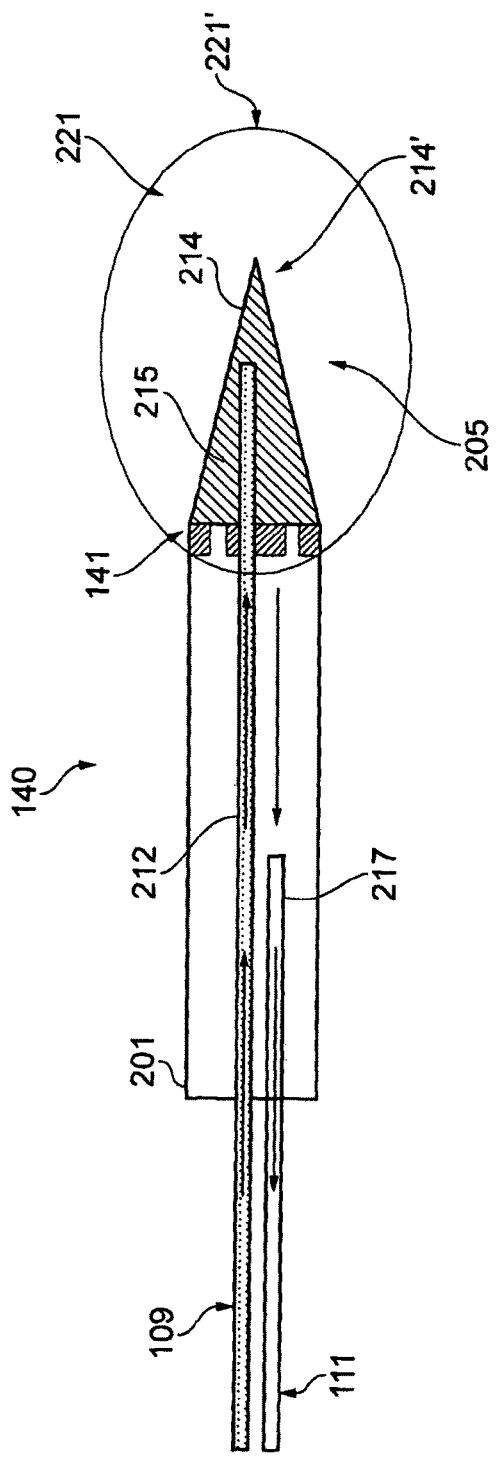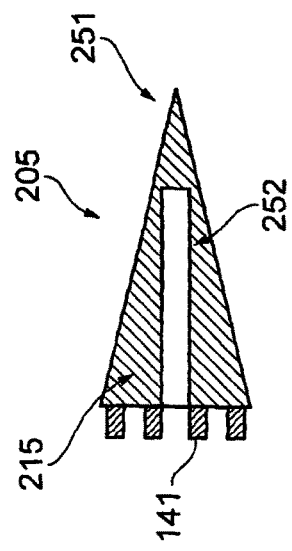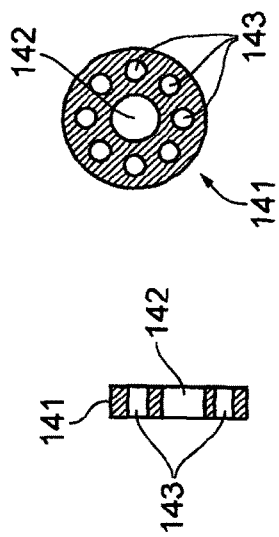
FIG. 10
FIG. 10a
FIG. 10b

APPARATUS, PROBE AND METHOD FOR A CRYOGENIC SYSTEM

CROSS REFERENCE TO RELATED APPLICATIONS

This application is a national stage application of International Application No. PCT/GB2012/052700, filed 30 Oct. 2012, from which application priority is a claimed, and which is incorporated herein by reference.

The present invention relates to an apparatus, probe and method for a cryogenic system, specifically, though not exclusively for cryosurgery and components and parts thereof.

Cryosurgery is the controlled destruction of unwanted tissue by the application of extreme cold. The extreme cold causes water in cells to freeze and this freezing kills the cells. Cells are known to be killed after exposure to temperatures below −20° C. It is known to use cryogenic systems in cryo-ablation and cryo-analgesia surgeries.

Cryosurgery is a well-established clinical technique for treating common soft tissue tumours in cancer cases involving the liver, kidney, prostate, breast and lung. Cryosurgery enables tumours, which are regarded as inoperable by other means, to be treated with excellent postoperative morbidity. More recently, the technique has expanded into other fields including podiatry for treating conditions such as Morton's Neuroma and Plantar fasciitis. Cryosurgery Neuroablation is an effective, safe, minimally invasive clinically proven procedure that can be performed in the office setting.

Cryogenic systems for surgical applications generally use one of two distinct mechanisms to achieve the required cooling.

At present the favoured cryo-surgery mechanism uses a Joule-Thompson device. These devices rely on the Joule-Thompson effect to induce cooling by expansion of a high pressure gas (e.g. $N_2O$) through a small orifice. Such devices require the deployment of high pressure gas in vivo. The high pressure gas is delivered to an expansion orifice within the probe, where the gas expands to produce the required cooling via the Joule-Thompson effect. If the gas escapes into the patient serious damage may be done. Clearly containment is a serious issue, gaseous matter within the body can be seriously damaging. A jet of compressed gas at 1500 psi escaping from even a very small hole would cause significant damage to soft tissue structures. Additionally if such gaseous matter makes its way to the heart via the cardiovascular system as cardiac arrest may result.

Further, these systems are very expensive for three principal reasons. Firstly, to achieve low temperatures the mixture of gases used are expensive. Secondly, the probes used with these systems are for single use only, primarily because manufactures are reluctant to certify probes for multiple uses which must contain high pressure gasses in vivo. Third, the Joule-Thompson effect provides a limited cooling capacity, that is—whilst Joule-Thompson devices may obtain low temperatures their capacity to absorb heat is limited by the (relatively small) amount of energy absorbed by an expanding gas. Due to this limited cooling capacity Joule-Thompson devices may require several probes for each treatment. Further, each probe may cost up to several thousand dollars. This gives a total treatment cost of tens of thousands of dollars per treatment, in probes alone.

Liquid cryogenic devices rely on evaporation of a liquid, such as liquid nitrogen or helium, to produce cooling by boiling and/or evaporation. The capacity of liquid cryogenic systems to absorb heat is vastly superior to the capacity of Joule-Thompson devices to absorb heat. This is because the latent heat of vaporisation for most cryogenic fluids commonly used in liquid cryogenic systems is significantly greater than the heat absorbed by the expanding gas(es) commonly used within Joule-Thompson systems.

Currently, there may be a surgical perception that liquid cryogenic systems can take too long to reach the temperatures required for cryosurgery. Prior art devices attempt to increase cooling speed by pressurising the liquid nitrogen feed (for instance to 275-415 kPa nominal). However, once the surgeon has initiated the system the probe can still take several minutes to begin cooling.

When a prior art liquid cryogenic device is operated (from warm) it exhibits phasing within the feed line whilst the feed line is cooling to operating temperatures. As the cryogenic liquid comes into contact with a warm (by which is meant above the boiling point of the cryogenic liquid) portion of the delivery line the cryogenic liquid boils and/or evaporates. When liquid nitrogen boils and/or evaporates the phase change results in an approximately 700 fold increase in volume which hinders the flow of liquid nitrogen through the feed line. Slugs of liquid nitrogen and gas travel along the feed line until the line cools sufficiently to permit the continual flow of cryogenic liquid. Clearly, the compressibility of the slugs of gas between slugs of incompressible liquid inhibits passage of the liquid. These effects result in efficiency losses, leading to an increase in the time between a surgeon or other operative starting the device and the device achieving a satisfactory operational state. The prior art devices attempt to overcome this phasing by pressurising the liquid nitrogen to encourage faster cooling of the feed lines by the liquid nitrogen. This can lead to complication of the feed system and usually does not overcome in total the issues described above.

The present invention is as set out in the independent claims.

It is an object of certain examples of the present invention to provide an improved apparatus and method for liquid cryogenic systems. Various examples seek to overcome, or at least substantially reduce, the disadvantages associated with the known liquid cryogenic systems discussed above.

According to at least some examples of the invention there is provided an apparatus (101) for cryosurgery comprising: an exhaust line (111,211) configured to receive cryogen (103) from a probe (105); and a suction/vacuum source (107) of reduced, e.g. sub-atmospheric, pressure configured to be in fluid communication with the exhaust line (111,211).

According to at least some examples of the invention there is provided a probe (105) for cryosurgery comprising: a dispersive medium (215) configured such that, in use, cryogen (103) delivered to the probe disperses within the probe through the dispersive medium.

According to at least some examples of the invention there is provided a method and a means (109,209,211,111,107) for drawing cryogen (103) from a cryogen source for delivery to a probe (105) using a vacuum source (107).

According to at least some examples of the invention there is provided a method and a means (209,215,211) for dispersing, within a probe (105), cryogen (103) delivered to the probe through a dispersive medium (215).

According to a first aspect of the disclosure, there is provided liquid cryogen cryosurgery apparatus or apparatus for cryosurgery comprising a source of liquid cryogen, a delivery line for delivering liquid cryogen to a probe, an exhaust line for receiving cryogen from a probe, a vacuum source in fluid communication with the exhaust line.

This liquid cryogenic system enables more efficient cooling of the probe than that provided by the prior art, by overcoming, or at least substantially reducing, phasing and its associated drawbacks.

A vacuum reservoir may be provided upstream of the vacuum source. The vacuum reservoir may be in communication with a heat exchanger, heating element or other cryogen heating means.

A second aspect of the disclosure provides a liquid cryogen exhaust apparatus, comprising a vacuum source, an upstream vacuum reservoir, and a cryogen heating means upstream of the vacuum source.

Preferably and conveniently the cryogen heating means is located within the vacuum reservoir.

According to a third aspect of the disclosure, there is provided cryogen line for liquid cryosurgery apparatus, the line comprising a supply conduit for the supply of liquid cryogen and a concentric insulating line, the insulating conduit being continuously evacuable by a vacuum source.

In one example a cryogen exhaust conduit, e.g. for the exhaust of cryogen, is provided in the line, preferably concentrically between the supply conduit and insulating conduit.

Thermally insulating spacers may be present in parts of the line outside the supply conduit, e.g. in the insulating conduit and/or in the exhaust conduit. Spacers may be fabricated from glass, ceramics, plastics or other materials resistant to damage from thermal cycling and or the conditions found under autoclave or other cleaning/sterilising regimes.

Another aspect of the disclosure comprises a flexible line for the supply of cryogen in a cryosurgery apparatus, the line comprising an array of articulated members of low thermal conductivity, each having a passage there through for the flow of cryogen.

A further aspect of the disclosure provides a probe for cryosurgery, for example for liquid cryosurgery, the probe comprising a proximal end for connection to a cryogen delivery line and a thermally conductive distal end for effecting cryosurgery, the probe comprising a cryogen supply line and a cryogen exhaust line, the exhaust line being provided concentrically about the supply line and along the entire length thereof.

The probe may also comprise a concentric peripheral insulating conduit, being provided around the exhaust line and being continuously evacuable.

A further aspect of the disclosure provides a probe for cryosurgery, for example for liquid cryosurgery, the probe comprising a proximal end for connection to a cryogen delivery line and a thermally conductive distal end for effecting cryosurgery, the probe comprising a cryogen supply line and an insulating conduit, the exhaust line being provided concentrically about the supply line and being continuously evacuable.

A yet further aspect of the disclosure provides a liquid cryogen cryosurgery apparatus or apparatus for cryosurgery comprising a primary source of liquid cryogen and a secondary source of liquid cryogen, the primary source supplying the secondary source with liquid cryogen, cryogen being deliverable from the secondary source to a probe whilst the primary and secondary sources are in fluid communication to effect cryosurgery.

Preferably, the secondary source is filled with cryogen from the primary source prior to commencing cryosurgery.

Preferably, a conduit between the primary and secondary sources is permanently insulated, e.g. it comprises a conduit with a permanent vacuum jacket and/or other insulation. The conduit between the primary and secondary sources may be less than 2 m, say less than 1.75, or 1.5, 1.4, 1.3, 1.2, 1.1 or 1.0 m in length. A conduit between the secondary source and the probe may be less than 2 m, say less than 1.75, or 1.5, 1.4, 1.3, 1.2, 1.1 or 1.0 m in length.

The secondary source may comprise a thermocouple or other content measuring device. Preferably the content measuring device may be operable to automatically control the flow of cryogen from the primary to secondary source.

A further aspect of the disclosure provides a method of supplying a cryogen to a heat exchanger/probe, the method comprising providing a source of vacuum to draw cryogen from the heat exchanger/probe. Optionally, though not essential, the method may further comprise pressurising a source of cryogen to force cryogen to a heat exchanger/probe.

Still further aspects of the disclosure relate to methods of effecting cryosurgery using the apparatus described herein.

In order that the invention may be more fully understood, preferred examples in accordance with the invention will now be described, by way of example only, and with reference to the accompanying drawings in which:

FIG. 6 is a cross-sectional schematic view of an alternative tri-axial line for use with an example of the present invention;

FIGS. 10, 10A and 10B are schematic views of an alternative probe for use with an example of the present invention.

Figure 1:
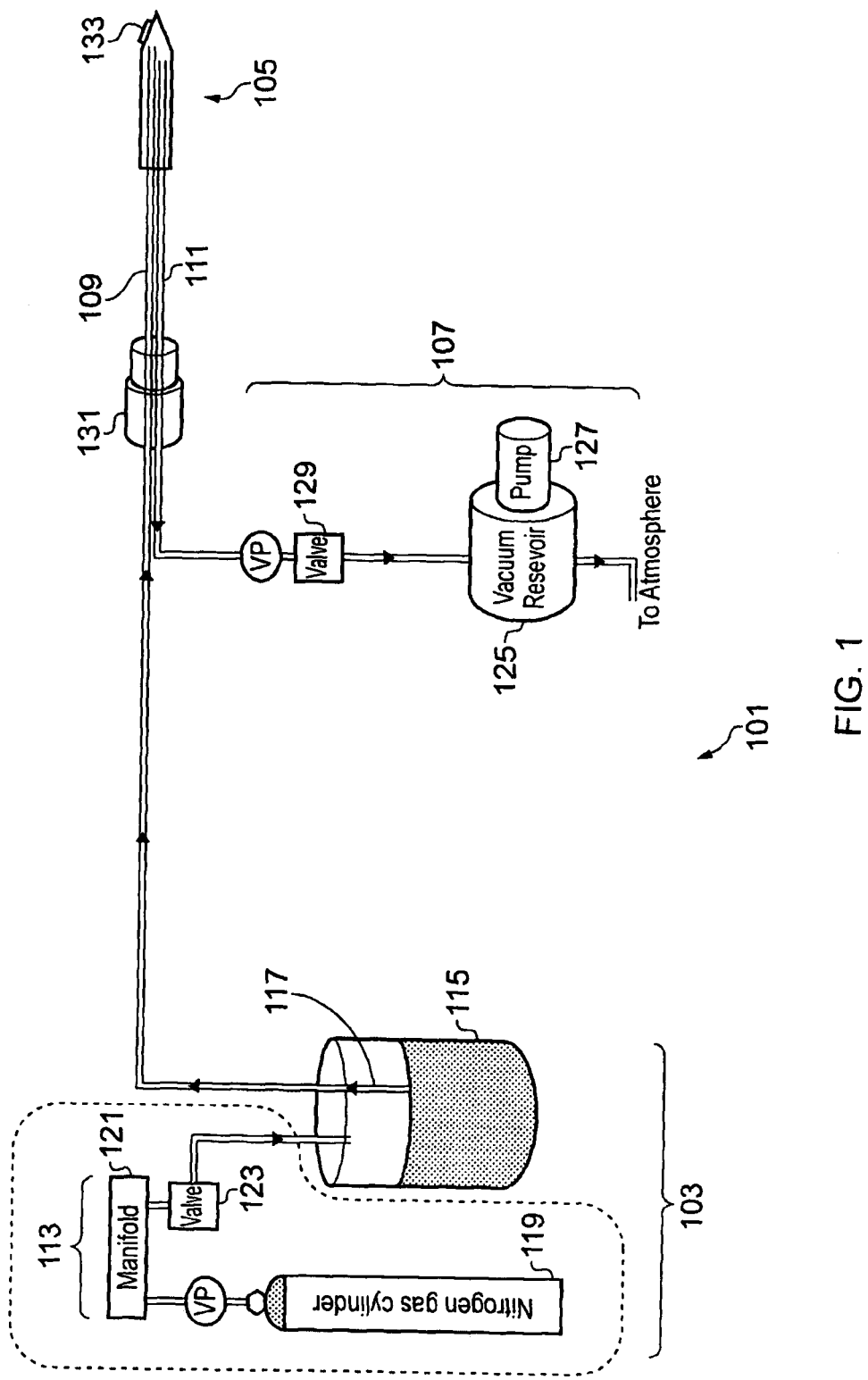
FIG. 1 is a schematic view of a cryogenic system according to an example of the present invention.

Referring firstly to FIG. 1, a cryogenic system, indicated generally at 101, comprises apparatus for supplying liquid cryogen 103, a probe 105, and a vacuum source 107. The apparatus for supplying liquid cryogen 103 is connected to the probe 105 by means of delivery line 109. The probe 105 is also connected to the vacuum source 107 by means of exhaust line 111.

In various examples, the vacuum source 107, i.e. source of negative pressure compared to that of atmospheric pressure, is configured such that it can suck or draw the liquid cryogen to the probe 105. Advantageously, this avoids, or reduces the need to provide a pressure source, i.e. a source of positive pressure compared to that of atmospheric pressure, to force the liquid cryogen to the probe.

The apparatus for supplying liquid cryogen 103 may comprise a source of liquid cryogen which is drawn to the probe 105 via the vacuum source 107.

Optionally however, as shown in FIG. 1 with reference to the components in the dotted line, in one example the apparatus for supplying liquid cryogen 103 (which may be that as described in WO 96/30816) may comprise a means for supplying propellant gas 113, a Dewar 115, and a pipe 117 which, in use, has an end beneath the surface of the liquid cryogen. The means for supplying a propellant gas 113 comprises a nitrogen gas cylinder 119, which is connected to a manifold 121. The manifold 121 is connected to a valve 123, the valve 123 is operable to regulate the pressure of the propellant gas. The valve 123 is connected to the Dewar 115. In use, propellant gas is fed above the surface of the liquid cryogen contained within Dewar 115. The Dewar 115 is configured such that, in use, the pressure of the propellant gas may displace liquid cryogen along the pipe 117. The pipe 117 has, in use, one end beneath the surface of the liquid cryogen contained within the Dewar 115 and the other end is connected to delivery line 109. The provision of such a means for applying pressure to the liquid cryogen to force it through the delivery line 109 to the probe 105 is not essential. Instead, other examples rely on the provision of a downstream vacuum or reduced pressure source to draw up/suck the liquid cryogen to the probe 105.

Figure 2:
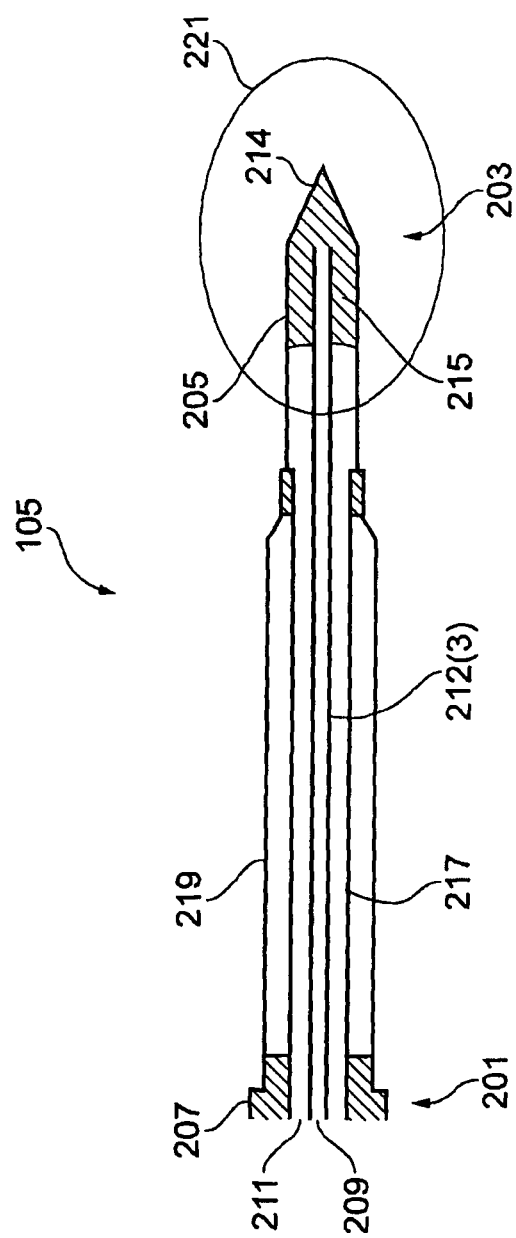
FIG. 2 is a cross-sectional schematic view of a probe for use with an example of the present invention.

A probe 105 for use with an example of the present invention is shown in more detail in FIG. 2.

The probe 105 comprises a proximal end 201 and a distal end 203. At the proximal end 201 of probe 105 is a fitting 207 for connection to the delivery line 109 and the exhaust line 111. The fitting 207 comprises an inlet 209 and an outlet 211. In use, the inlet 209 is connected to delivery line 109 and the outlet 211 is connected to the exhaust line 111.

The inlet 209 is also connected to, that is in fluid communication with, tip 205 at the distal end 203 of the probe 105 by means of a delivery tube 212. Thus, in use, liquid cryogen may flow from the delivery line 109 to the probe tip 205 at the distal end 203 of the probe 105 via inlet 209 and delivery tube 212.

The probe tip 205 is thermally conducting. It may also be impermeable or semi-permeable to liquid cryogen. Thus, the probe tip 205 is operable as a heat exchanger. The outer surface 214 of tip 205 is of a thermally conducting substance, for example gold (chosen for its conductivity and sterilisability). Within tip 205 is a region 215 of a dispersive medium through which the cryogen is delivered/passed through for dispersal. The dispersive medium 215 provides a plurality of nucleation sites for the liquid cryogen, to encourage nucleation, boiling and/or evaporation of the liquid cryogen passing therethrough to effect optimal thermal transfer and heat exchange. The dispersive medium is thermally coupled/in thermal communication with the outer surface 214 of the probe tip 205. In use, the dispersive medium and the outer surface 214 of the probe tip, are cooled due to liquid cryogen's boiling and/or evaporation when in contact with the dispersive medium 215. The dispersive medium may be formed of a thermally conductive and porous material. The dispersive medium may be formed of a sintered material. The sintered material may be a sintered: metal (such as at least one of: Aluminium, Copper and Bronze or other metals), ceramic, plastic or any other material suitable for sintering.

Of course, other materials which provide plural, preferably tortuous, passageways for the passage of cryogen and the boiling thereof to enhance the dispersion of the cryogen throughout the dispersive medium, may be used for the dispersive medium.

The probe 105 also comprises an exhaust tube 217, which connects the probe tip 205 to the outlet 211. Thus, the inlet 209 and outlet 211 are in fluid communication via the dispersive medium region 215 within the tip 205 at the distal end 203 of the probe 105.

A high volume of gas may be generated in the probe tip following boiling/evaporation of the liquid cryogen. For example, liquid nitrogen has an expansion ration of approximately 700 to 1. Advantageously, a porous, dispersive and diffusive medium enables the cryogen, having transformed from a liquid to a gaseous state, to pass through the dispersive medium and out through the outlet 211 and exhaust line 111.

Probe 105 also comprises insulated region 219. The insulation may be provided by one or more of a vacuum, partial vacuum, or other means such as a material with low thermal conductivity. In use, this region may be in contact with tissue which is not to be damaged by the extreme cold of the cryosurgery. The insulated region 219 may be fabricated to allow cleaning of the probe 105, e.g. by autoclaving. For example the insulated region 219 may be removable or made from cleaning-resistant materials, a cleanable probe is likely to be re-usable.

In use, with the present cryogenic system 101 the probe insulating region 219 may be evacuated by the vacuum source 107.

The probe 105 is also connected to the vacuum source 107. The exhaust line 111 is connected to the outlet 211 of the probe 105. The exhaust line 111 is connected to a vacuum reservoir 125 and a pump 127 via valve 129. The pump 127 is operable to produce a vacuum within reservoir 125. The vacuum pump 127 vents to the atmosphere, generally via a scavenging connection to meet safety requirements. The valve 129 is operable to control the vacuum supplied by the pump 127 and reservoir 125 to the exhaust line 111. In use, the exhaust line 111 supplies means for supplying propellant gas 113 a vacuum to the probe 105 and the probe 105 in turn supplies vacuum to the delivery line 109. Accordingly, the liquid cryogen can be urged/drawn/sucked through the delivery line 109 to the probe tip via a lifting effect on the source of the liquid cryogen due to a vacuum "down-stream" of the probe tip, e.g. in the exhaust side of the system, rather than using a source of positive pressure "up-stream" of the probe tip, e.g. in the delivery side of the system. Advantageously, the use of a porous permeable dispersive medium, such as a sintered material, enables the lifting effect of the "down-stream" vacuum/suction to pass therethrough, thereby communicating the vacuum/suction to the liquid cryogen source via the delivery line. Thus, examples of the invention enable the use of negative pressure compared to that of atmospheric pressure to draw up the liquid cryogen to the probe tip rather than positive pressure to force the liquid cryogen to the probe tip. One can consider that examples of the invention enable the liquid cryogen to be delivered to the probe tip by being "sucked" along to the probe tip by a vacuum or source of reduced (sub-atmospheric) pressure down-stream of the probe tip rather than relying on active pressure applied up-stream of the probe tip (as occurs in previous cryogenic systems).

The apparatus for supplying liquid cryogen 103 and the vacuum source 107 may be located within a common housing.

Previous cryogenic systems required a pump on a delivery side to create a positive pressure to force liquid coolant to the probe tip. Examples of the present invention enable a pump at an exhaust side to be used instead to create vacuum (negative pressure) to cause the liquid coolant to be drawn to the probe tip.

Previous cryogenic systems suffered the drawback in that, on the delivery side the pump and its associated fluid communication lines and valves had to contend with liquid cryogen. Whereas with examples of the present invention, the pump and its associated fluid communication lines and valves only need handle the cryogen in its gaseous form. The gaseous cryogen is at a much higher temperature than liquid cryogen. Therefore, examples of the present invention enable the vacuum source pump, and its associated fluid communication lines and valves, to operate at much higher temperatures than prior art.

Figure 3:
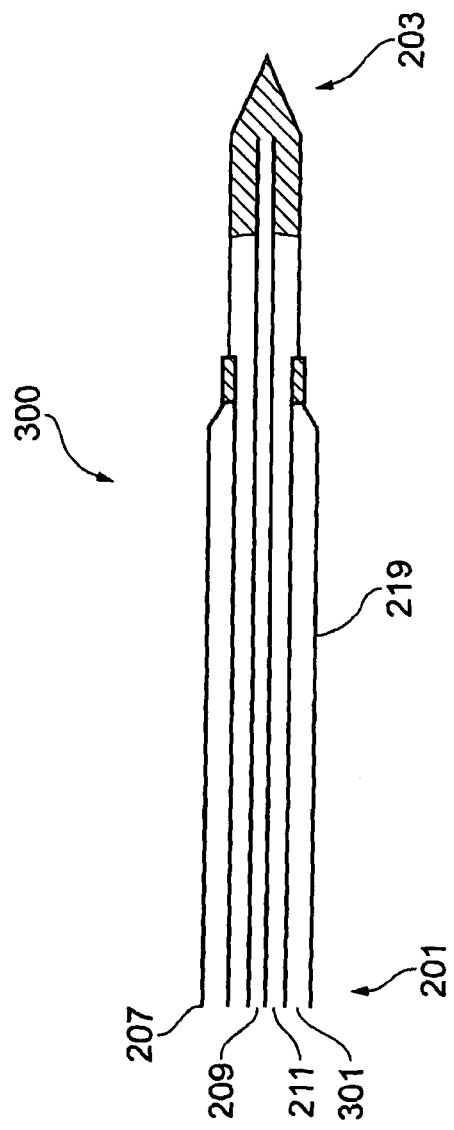
FIG. 3 is a cross-sectional schematic view of an alternative probe for use with an example of the present invention.

An alternative probe 300 is shown in FIG. 3. The alternative probe 300 is similar to that described and shown in FIG. 2, only the differences will be described. The alternative probe 300 comprises at the proximal end 201 an additional port 301 within the fitting 207. The fitting 301 is connected to vacuum insulated region 219. In this way, it is not necessary to provide a probe 105 which is capable of holding a vacuum within region 219 for the entire lifetime of the probe 300. Vacuum insulation for region 219 may be supplied by vacuum source 107 via port 301. Because there are no sealed portions the probe 300 is capable of cleaning, e.g. by autoclaving and is thus capable of re-use.

Figure 4:
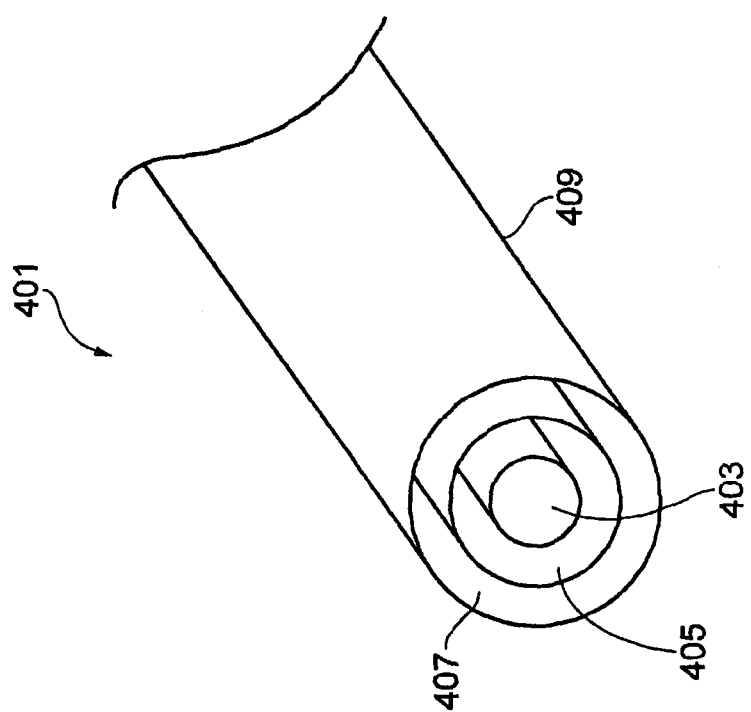
FIG. 4 is a schematic view of a tri-axial line for use with an example of the present invention.

Shown in FIG. 4 is a tri-axial line 401 for use with an example of the cryogenic system 101. The tri-axial line 401 may be present from the connector 131 to the probe 105 only or used elsewhere within the cryogenic system 101. The tri-axial line comprises a feed line 403, an exhaust line 405 and an insulating line 407. The feed line 403 is within the exhaust line 405 which, in turn, is within the insulating line 407.

The exhaust line 405 and the insulating line 407 act together to reduce undesirable condensation on the outside 409 of the tri-axial line 401 and reduce evaporation losses from the supply of cryogen via the feed line 403.

In this example a vacuum, preferably from the vacuum source 107 is applied to the insulating line 407. The vacuum may be provided via a split or controllable flow so that a greater vacuum is applied to one or other of the exhaust 405 and insulating 407 lines.

Figure 5:
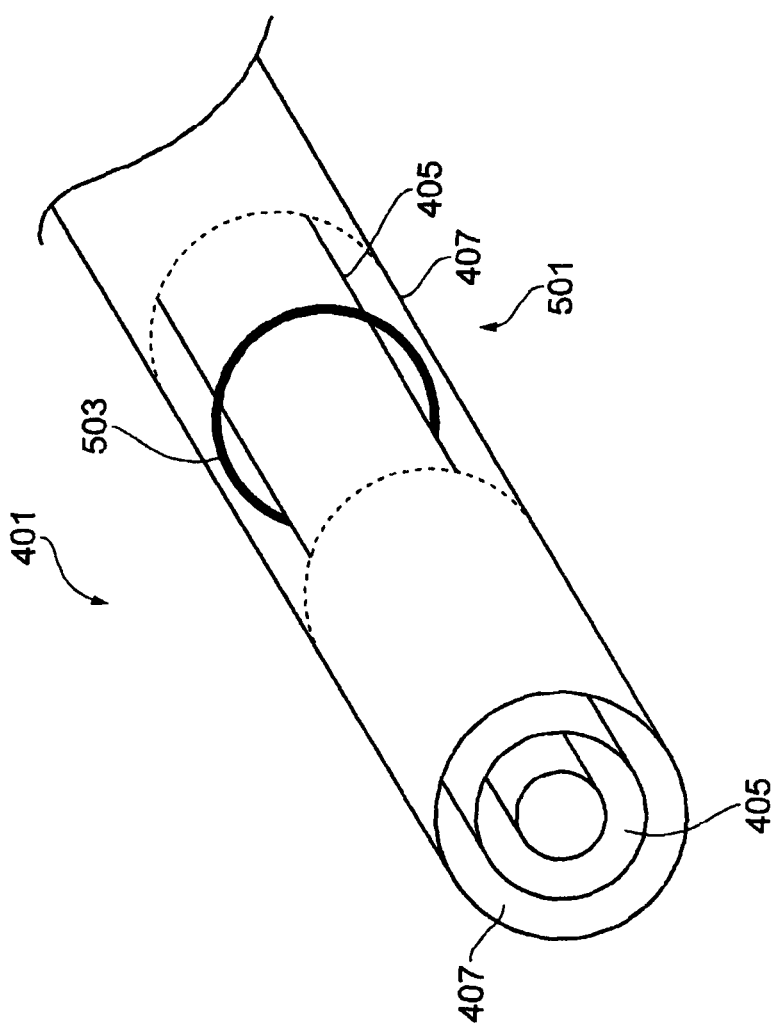
FIG. 5 is a schematic view of the tri-axial line of FIG. 4 showing a cut away section.

FIG. 5, which is an alternative view of the tri-axial line 401, having a cutaway section 501 for illustrative purposes only, shows that the tri-axial line 401 comprises a spacer 503. The spacer 503 is within insulating line 407. The spacer 503 is made of an insulating material, for example glass or ceramics. The spacer 503 acts to prevent the exhaust line 405 from touching the insulating line 407. In this way the effectiveness of the insulating line 407 is increased. Performance is markedly increased when the tri-axial line 401 is bent, as in this formation the spacer 503 prevents the exhaust line 405 from touching the insulating line 407. The spacers 503 are positioned along the length of the tri-axial line. They may be any shape but they must allow the passage of fluids so as not to inhibit exhaust flow and so on.

FIG. 6 shows an alternative tri-axial line 601 in cross sectional schematic view. The alternative tri-axial line 601 also comprises a central delivery line 603, an exhaust line 605 and a peripheral insulating line 607. However, the insulating line 607 does not have a separate connector at the end of the line 601. Instead, vacuum is provided within insulating line 607 by the vacuum supplied to exhaust line 605. This vacuum is supplied by means of valve 609, valve 609 permits flow of fluids from insulating line 607 to exhaust line 605 only. In this way any vacuum applied to exhaust line 605 will become present in insulating line 607, however, if insulating line 607 comprises a vacuum and an exhaust line 605 is pressurised relative to insulating line 607 then the vacuum in insulating line 607 will remain substantially intact. The alternative tri-axial line 601 also features insulating spacers 503.

The tri-axial lines 401, 601 are advantageous as the boil off, which is at a temperature between the temperature of the cryogenic liquid and the ambient temperature, provides a layer of insulation between the delivery line 403, 603 and the insulating line 407. This insulation is provided by cold gases, that in prior art systems would have merely been vented to the atmosphere. As will be appreciated, on start up the cold gas flowing from the probe will help to cool the delivery line 603 as cryogen is supplied. The vacuum in the insulating line 607 will help to ensure the insulation.

Further, these tri-axial lines 401, 601 are advantageous, as in order to allow for re-use of a line in surgery it must be sterilisable. Sterilisation is generally accomplished by autoclaving, which consists essentially of high pressure and temperature steam treatment. The present tri-axial lines 401, 601 mitigate the need to provide an insulating line capable of maintaining a vacuum after several autoclave cycles.

Figure 7A:
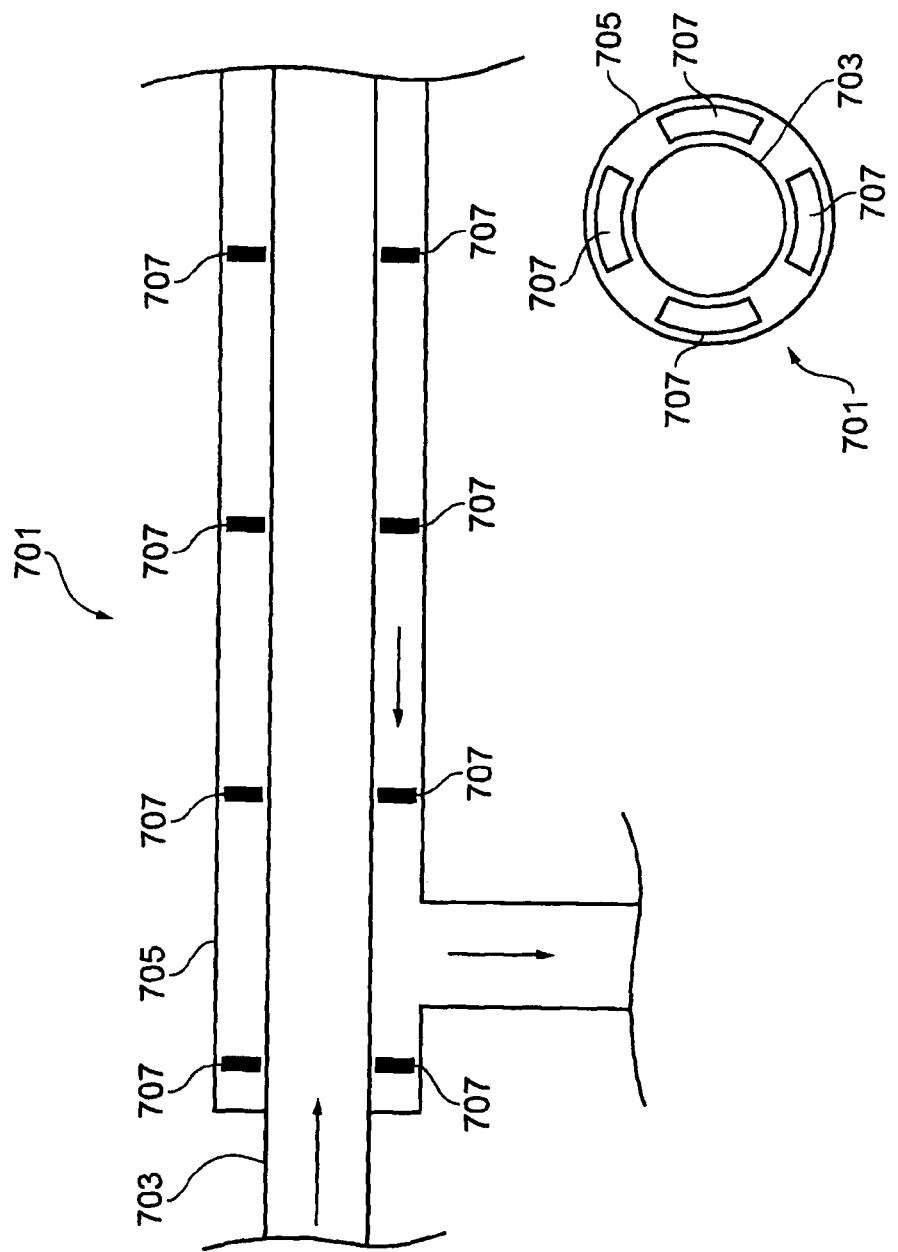
FIG. 7A is a cross-sectional schematic view of a bi-axial line for use with an example of the present invention.

FIG. 7A shows an alternative line 701 in schematic cross-sectional view for use with examples of the present invention. The alternative line 701 is a bi-axial line, and comprises a central delivery line 703 and an exhaust line 705. The delivery line 703 is within the exhaust line 705. The exhaust line 705, in use, carries cold boil off away from the probe. Hence, in use, the cold boil off acts to insulate delivery line 703 from ambient temperatures. This reduces undesirable condensation on the outside of the bi-axial line 701 and evaporation losses from the supply of cryogen via the delivery line 703. The exhaust line 705 may be of a flexible material, such as silglass, accordingly, spiders 707 or other suitable spacers may be provided to prevent the exhaust line 705 completely collapsing under vacuum, when used with the present invention.

Figure 7B:
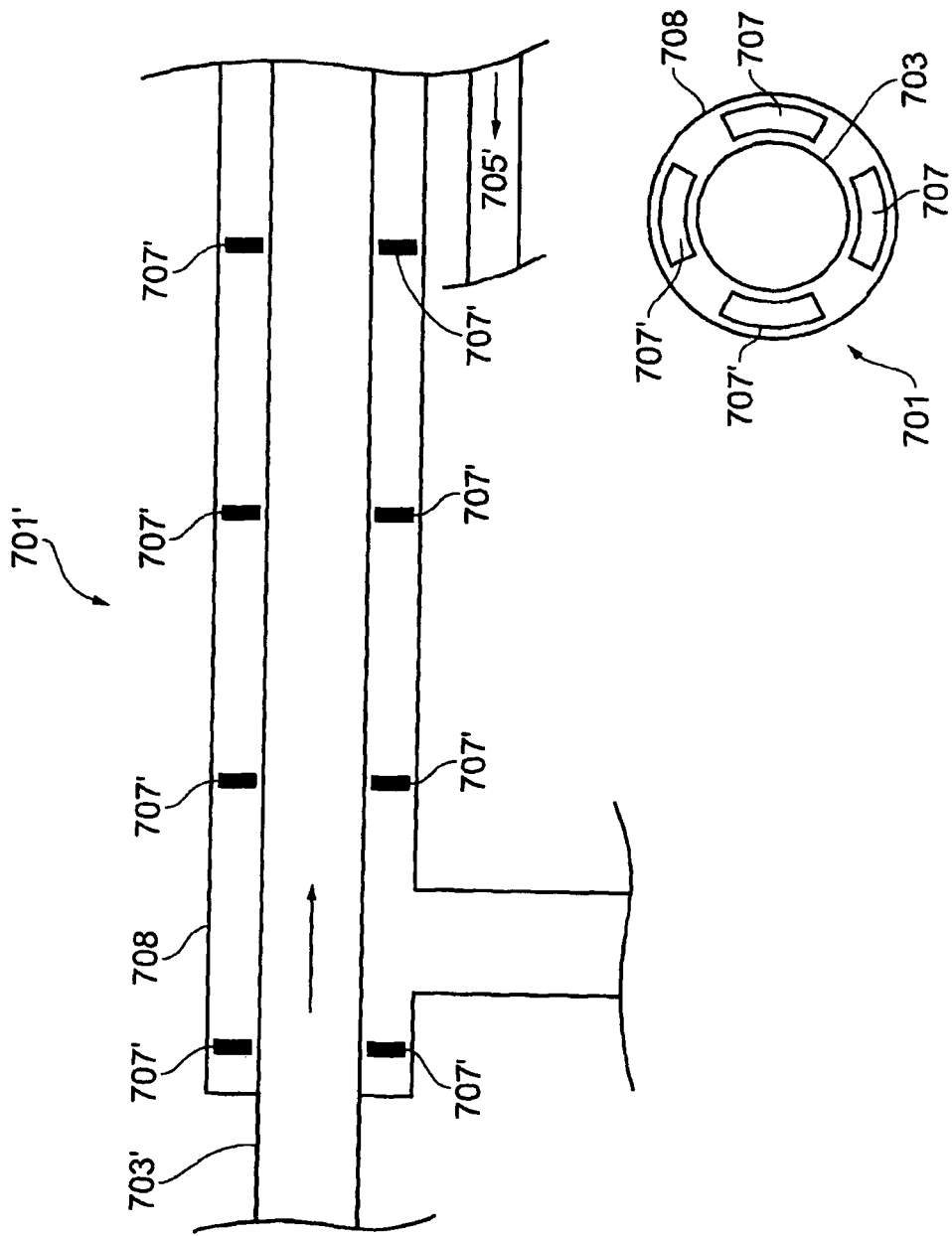
FIG. 7B is a cross-sectional schematic view of an alternative bi-axial line for use with an example of the present invention.

FIG. 7B shows an alternative example of line 701' the supply line 703' can be surrounded by an insulating line 708. A separate exhaust line 705' is provided to take nitrogen gas from the probe tip. In this example the insulating line has a vacuum applied thereto. Preferably the vacuum is provided by the vacuum source in communication with the exhaust line 705'.

Figure 8:
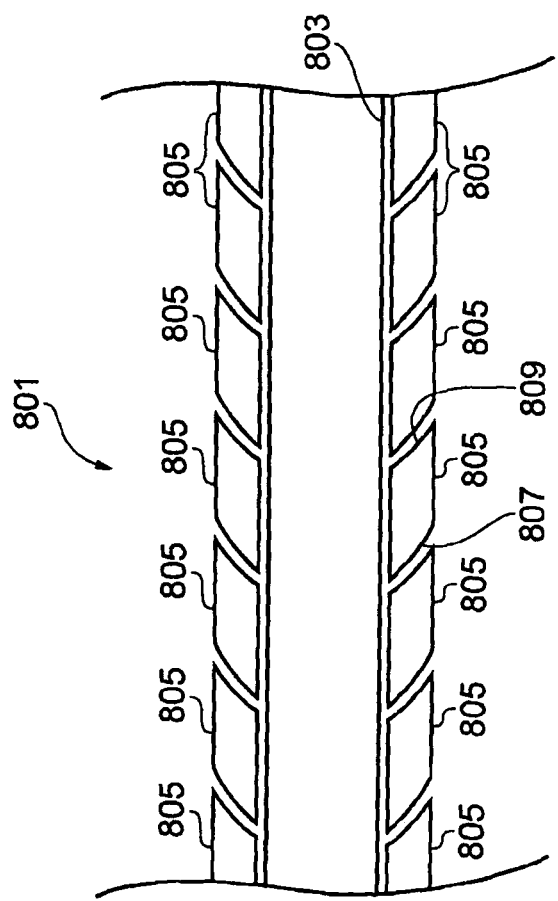
FIG. 8 is a cross-section schematic view of an insulated delivery line for use an example of with the present invention.

FIG. 8 shows an alternative delivery line assembly 801 in schematic cross-sectional view for use with the present invention. The delivery line assembly 801 comprises a delivery line 803, which is insulated by means of ceramic collars 805.

The ceramic collars 805 lie adjacent each other and cover substantially the whole length of the feed line 803. The ceramic collars 805 have a concave curved portion 807 at one end and a convex curved portion 809 at the other end. The concave curved portion 807 of one ceramic collar is complementary with a convex curved portion 809 of another, such that the delivery line 803 may be bent and still substantially insulated by the ceramic collars 805.

The ceramic collars 805 may be glazed, such that they are impermeable. Such glazed ceramic collars are more hygienic than unglazed ceramic collars. The delivery line assembly 801 is durable and can be sterilised by means of an autoclave, accordingly, such delivery line assemblies 801 are advantageous.

Any of the tri-axial line 401, the alternative tri-axial line 601, the alternative bi-axial line 701 or the delivery line assembly 801 may be used with any of the described cryogenic systems.

Figure 9:
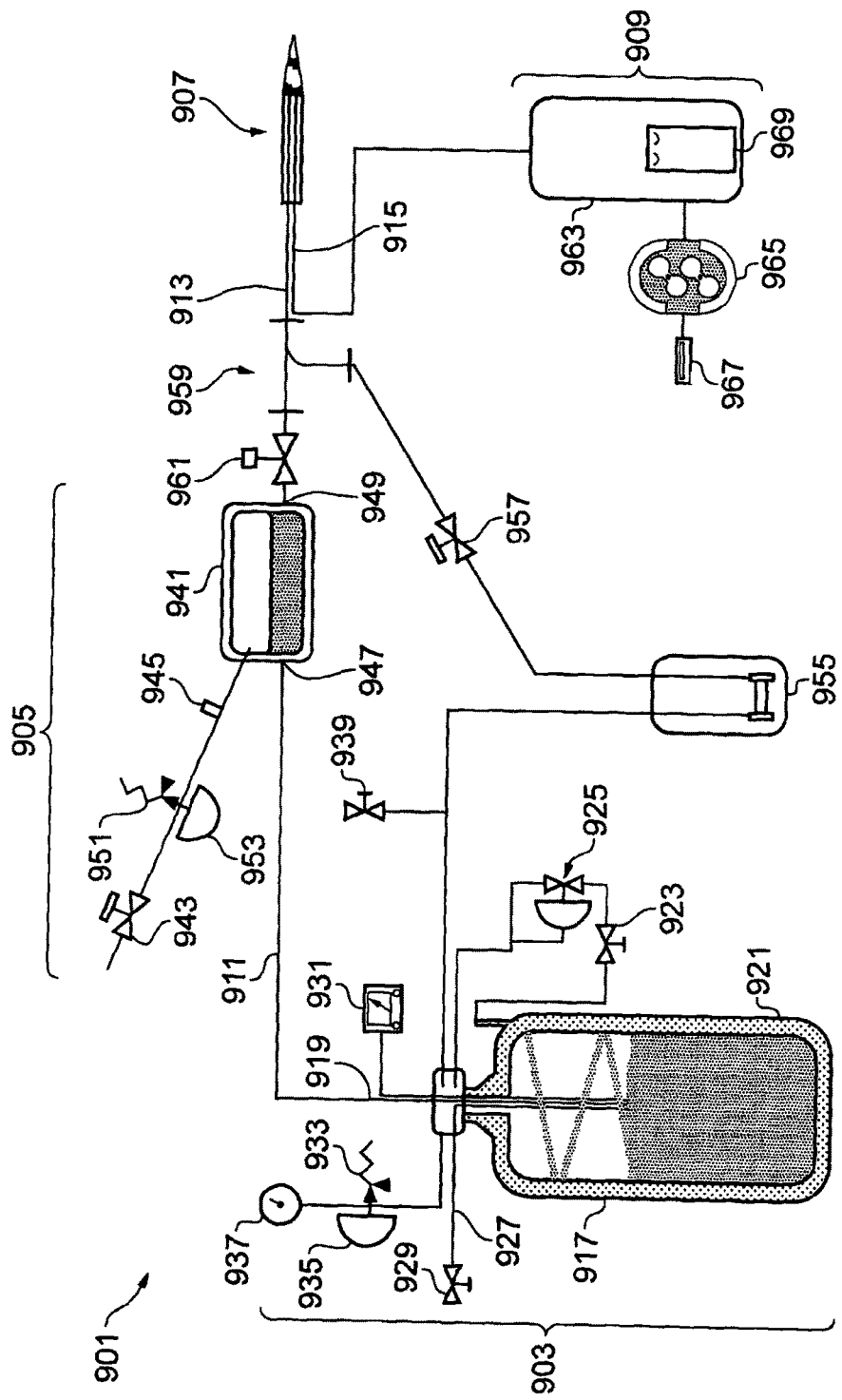
FIG. 9 is a schematic view of an alternative cryogenic system according to an example of the present invention.

FIG. 9 shows a further cryogenic system, indicated generally at 901. The cryogenic system 901 comprises apparatus for supplying liquid cryogen 903, an intermediate cryogen storage apparatus 905, a probe 907, and a vacuum source 909. The apparatus for supplying liquid cryogen 903 is connected to the probe via supply line 911, intermediate cryogen storage apparatus 905, and delivery line 913. The probe 907 is also connected to the vacuum source 909 by means of exhaust line 915.

The apparatus for supplying liquid cryogen 903 (which may be that as described in WO 96/30816 the entire disclosure of which is included herein by reference) comprises a means for supplying propellant gas, a Dewar 917, and a supply pipe 919 which, in use, has an end beneath the surface of the liquid cryogen. The Dewar 917 may be of any appropriate size and may be approximately 60 litres. The means for supplying a propellant gas comprises a pressure raising coil 921, an automatic pressure control valve 923, and a pressure control regulator 925. The pressure raising coil 921 is connected to the automatic pressure control valve 923 which is operable to regulate the pressure of the propellant gas by the user. The pressure control valve 925 is connected to the pressure control regulator 925. The pressure control regulator 925 is operable to maintain a preset propellant gas pressure within the Dewar 917 when the pressure control valve 923 is open. The preset propellant gas pressure may be of any appropriate value, e.g. 414 kPa (60 psi). The pressure control regulator 925 is connected to Dewar 917. In use, propellant gas is fed above the surface of the liquid cryogen contained within the Dewar 917. The Dewar 917 is sealable such that, in use, the pressure of the propellant gas may displace liquid cryogen along the supply pipe 919. The supply pipe 919 has, in use, one end beneath the surface of the liquid cryogen contained within the Dewar 917 and the other end is connected to the supply line 911.

The apparatus for supplying liquid cryogen 903, also comprises a fill line 927 and fill valve 929 for filling the Dewar 917 with liquid cryogen. The apparatus for supplying liquid cryogen 903 also comprises a contents gauge 931, the contents gauge 931 is a capacitance contents gauge which displays the remaining contents and communicates this value, for example to a control system. The apparatus 903 further comprises a safety relief valve 933 and a bursting disc 935 to prevent the apparatus 903 from reaching an excessive pressure. The apparatus 903 further comprises a pressure gauge 937 which displays the system pressure and communicates this value, for example to a control system. The apparatus 903 also comprises a gas vent 939 to release pressure within the apparatus 903 when desired.

The cryogenic system 901 also comprises an optional intermediate cryogen storage apparatus 905 which connects the supply line 911 and the delivery line 913. The purpose of the intermediate cryogen storage apparatus 905 is to provide cryogen at a location nearer to the probe 907 than is possible in known prior art systems. Since the Dewar 917 of the apparatus for supplying liquid cryogen 903 has a volume of approximately 60 litres and a height of approximately 1 meter it is usually not possible for the apparatus for supplying liquid cryogen 903 to be in close proximity to the probe 907. The distance between the apparatus for supplying liquid cryogen 903 and the probe is typically 2 metres, the intermediate cryogen storage apparatus 905 is typically placed such that the supply line 911 and the delivery line 913 are 1 metre in length. However, the most important feature is to shorten the length of delivery line 913, such that the time from initiating cooling of the probe 907 to the probe 907 actually cooling is minimised.

The intermediate cryogen storage apparatus 905 comprises an intermediate Dewar 941. The intermediate Dewar 941 connects the supply line 911 and the delivery line 913, its purpose is to allow the supply line 911 to be cooled to liquid cryogen temperature before the delivery line 913. The supply line 911 may be vacuum insulated. Such vacuum insulation, e.g. provided by a permanently vacuum insulated line, further reduces losses, e.g. evaporative losses, of cryogen. The intermediate cryogen storage apparatus 905 includes a vent valve 943, a thermocouple 945, a connection 947 to the supply line 911 and a connection 949 via the delivery line 913 to the probe 907. The connection to the delivery line 949 must be beneath the surface of the liquid cryogen in use, such that liquid cryogen is able to pass along the delivery line 913. The thermocouple 945 and the vent valve 943 must be towards the top of the intermediate Dewar 941, such that the thermocouple 945 can sense when the intermediate Dewar 941 is approaching full and the vent valve 943 can vent gaseous cryogen and not liquid cryogen. The intermediate cryogen storage apparatus 905 also comprises a safety relief valve 951 and a bursting disc 953 to prevent the apparatus 905 from reaching an excessive pressure.

In use, liquid nitrogen is fed from the apparatus for supplying liquid cryogen 903, by the propellant gas along the supply line 911 to intermediate Dewar 941. Whilst the cryogenic fluid is fed along (initially warm, that is above the boiling point of liquid nitrogen) the supply line 911 it boils and/or evaporates and the boil off is vented through vent valve 943. Once the intermediate Dewar 941 fills with liquid cryogen, the thermocouple 945 begins to cool. Once a predetermined temperature is reached (approximately the boiling point of the liquid cryogen in use) the propellant gas pressure is removed and the vent valve 943 is closed. In this way the supply line 911 can be cooled in advance of initiating a freeze state of the probe 907. Once the vent 943 is closed the whole assembly functions as a delivery line in order to allow cryogen flow to the probe 907 valve 961 is openable.

The cryogenic system 901 also comprises means for warming the probe 907 as part of a thaw cycle. Connected to the apparatus is a heater 955 for heating nitrogen gas to thaw the probe. The heater 955 is connected to the delivery line 913 via a valve 957 and a three-way connection 959. There is also provided a valve 961 between the intermediate cryogen storage apparatus 905 and the three-way connection 959. With this arrangement by operation of the valves 961, 957 it is possible to supply either liquid cryogen or hot nitrogen gas to the probe 907 as desired. By providing appropriate connections to the heater 955 it is possible to flow heated gas in either direction around the apparatus, as may be preferable.

The probe 907 is connected to a vacuum source 909 by means of exhaust line 915. The vacuum source 909 comprises a vacuum tank 963, a pump 965 and a vent 967. The vacuum tank 963 also comprises a heater 969 within the base of the tank 963, the purpose of the heater 969 is to boil any liquid cryogen that may arrive in the vacuum reservoir 963.

Between three-way valve 959 and probe 907 the delivery line 913 and the exhaust line 915 may be adjacent. Accordingly, the lines 913, 915 may be any of the tri-axial line 401, the alternative tri-axial line 601, the alternative line 701 or the delivery line assembly 801.

In use, the probe 105 (or any of 105, 300, 901) is inserted by a surgeon (the user) into a patient such that the region (such as a tumor) to be cryo-ablated is adjacent or in contact with the thermally conducting region of the tip 205. The cryogenic system 101 is activated when desired by the surgeon which may be before the probe is located in vivo. When the system is activated the valve 123 opens and propellant gas pressure is applied to Dewar 115. In the operating condition Dewar 115 is sealed such that the propellant gas acts on the liquid cryogen within Dewar 115. Thus, liquid cryogen is forced along the pipe 117 towards delivery line 109. The liquid cryogen as it comes into contact with the warm (above liquid nitrogen temperature) pipe 117 and feed line 109 will boil and/or evaporate. This liquid cryogen boil-off is removed by application of a vacuum to delivery line 109 via probe 105 and exhaust line 111, this vacuum is supplied by vacuum source 107.

As with prior art systems if the tube 117 and delivery line 109 are warm (that is—above the liquid cryogen boiling point) the liquid cryogen once it enters the feed tube 117 and delivery line 109 will begin to boil and/or evaporate until the feed tube 117 and delivery line 109 are sufficiently cold. However, unlike prior art systems, when liquid nitrogen is fed along feed tube 117 and delivery line 109 the vacuum source 107 operates to provide a vacuum on exhaust line 111. The vacuum applied to exhaust line 111 is applied to the delivery line 109 and delivery tube 117 via the probe 105. Whereas, in prior art devices the boil off from liquid nitrogen coming into contact with warm feed tube 117 and delivery line 109 hinders the flow of liquid nitrogen along feed tube 117 and delivery line 109, the present invention literally "sucks off" the boil off via probe 105 and exhaust line 111. Thus application of vacuum overcomes, or at least substantially reduces, the negative effects of phasing experienced in prior art devices.

This improves freeze rates and hence times, and provides reduced variation of pressure and flow in successive uses. Reduced freeze rates are particularly advantageous, providing shorter operating times, which may be critically important for patients undergoing traumatic surgical procedures. The present invention may provide a probe which begins to cool after less than 2 minutes from initiation of a freezing cycle. Moreover, in the initial state the application of a vacuum ensures that air present in the conduits is swiftly drawn through the apparatus, thereby limiting the opportunity for liquefaction of the air or solidification of any water.

During initial operation (from warm) a large volume of nitrogen boils off and a high rate of evacuation is required, initially the system operates at a maximum flow of liquid nitrogen until a probe tip thermal couple 133 reports the maximum for each temperature of $-196°$ C.

However, once the delivery tube 117 and delivery line 109 have been reduced to working temperature the rate of liquid nitrogen supply and evacuation can be reduced.

Once the feed line 109 has cooled sufficiently along its length liquid cryogen arrives at the probe 105. The liquid cryogen arrives at inlet 209 and is fed along feed tube 212 from the proximal end of the probe 201 to the distal end of the probe 203. Thus the liquid cryogen arrives within the tip 205 of the probe 105. Here the liquid cryogen comes into contact with a dispersive medium such as a sintered bronze region 215 of the probe tip 205. The sintered bronze region 215 promotes boiling and/or evaporation by provision of nucleation sites. Once the liquid cryogen has boiled and/or evaporated it is removed via exhaust tube 217, exhaust port 211, exhaust line 111 and vacuum source 107. The boiling and/or evaporation of liquid cryogen in sintered bronze region 215 within the probe tip 205 cools the probe tip 205 to cryogenic temperatures.

The probe tip 205 which is thermally conducting is thus able to cool surrounding tissue. This freezes the water in surrounding tissue and forms an ice ball 221. Cooling cells below $-20°$ C. is known to kill them.

Several factors determine the size of the ice ball formed. These factors include both the temperature of the probe tip and the capacity of the probe 105 to remove heat from surrounding tissue. Thus, the sintered bronze region 215 is particularly advantageous as it promotes boiling and/or evaporation removing the latent heat of evaporation from the probe tip 205 and surrounding tissue, forming ice ball 221.

The flow rate of liquid cryogen is controlled by the pressure of propellant gas acting on the liquid cryogen within Dewar 115 and the vacuum applied by vacuum source 107. The vacuum supplied by vacuum source 107 is controlled by valve 129, the pump 127 operating intermittently to provide a predetermined vacuum level within vacuum reservoir 125. Preferably, significant quantities of liquid cryogen boil within sintered bronze region 215. That is—the flow rates are adjusted to favour boiling within region 215.

For example, if the probe 105 has and outer diameter of 5 mm and an inner diameter of 2 mm, once the probe is fully cooled the flow rate will be approximate between 5 and 6 litres per minute.

When the cryogenic system 101 is operating at its most efficient level all, or at least substantially all, of the liquid cryogen boils within the probe tip 205. Thus appropriate control of cryogen supply and vacuum application reduce wastage and ensure that the apparatus functions optimally.

During operation of the system 101 the size of the ice ball 221 grows. Once an ice ball 221 of a desired size is formed, the surgeon switches the system to thaw mode. In thaw mode, nitrogen gas is fed from nitrogen gas cylinder 119 to the heater which heats the nitrogen gas. The hot nitrogen gas is then fed along delivery line 109 to probe 105. The hot nitrogen gas displaces any liquid nitrogen remaining within the delivery line 109, probe 105 and exhaust line 111. Further, the hot nitrogen gas heats the probe tip 205. The sintered bronze region 215 having a large surface area readily absorbs heat from the nitrogen gas. Once the probe tip has thawed sufficiently it can be removed from the patient by the surgeon. The use of nitrogen as a purge gas (as opposed to, say, air) is preferably since it will only form nitrogen condensate (as opposed to water or other impure condensate).

Alternatively, the system 101 may be arranged and operated such that the hot purge gas flows in a reverse direction along exhaust line 111, through probe 105 and out of inlet line 109.

The system may also provide an auto clean function, which operates by venting high-pressure gas through the probe 105 in a reverse direction, along exhaust line 111 through probe 105 and exiting through delivery line 109 to remove obstructions in the lines and/or probe.

The components of the system may be controlled from a common control panel providing adjustability of flow according to surgical requirements and so on. The parameters may be controlled according to a set program according to surgical requirements.

The cryogenic system 901 is operates in a like manner to the cryogenic system 101. FIG. 10 shows a further example of a probe 140. The probe 140 is similar to that described and shown in FIG. 2 and equivalent reference numerals have been used. Only the differences will be described. The delivery tube 212 extends along the length of the probe 140, through a mounting spacer 141 and into the dispersive medium 215. As shown in FIG. 10a, the mounting spacer 141 comprises a central aperture 142 for mounting the delivery tube as well as enabling the delivery tube to pass therethrough into the dispersive medium. The dispersive medium acts as a porous delivery face for the cryogenic liquid. The mounting spacer 141 also comprises a plurality of further apertures 143 to allow egress of fluid, such as cryogenic gas generated from the cryogenic liquid boiling/ evaporating when coming into contact with the dispersive medium. The cryogenic gas is then able to be drawn out from within the probe body though exhaust line 217, which is in fluid communication with a vacuum source (not shown).

As shown in FIG. 10b, the probe tip 205 comprises an outer surface/housing 251 of a thermally conductive material, for example silver, which covers and hermetically seals the dispersive medium 215 within the probe. The sintered material is provided with a cavity 252 to receive an end of the delivery tube 212. The use of a sintered metal, such as copper or brass, as the dispersive medium provides thermal properties and a thermal conductivity which are advantageous in the exchange of heat between the cryogen, the dispersive medium and the outer surface of the probe tip.

In use, a cryogenic liquid is delivered through the delivery tube to the dispersive medium and boils/evaporates at nucleation sites therein. The resultant cryogenic gas is then expelled from the probe via the exhaust tube and drawn away by a vacuum from a vacuum source located on the exhaust side of the system. However, not only can the vacuum source be used simply to draw the cryogenic gas away from the dispersive medium and out of the probe, but also, in certain examples of the invention, the cryogenic system is configured such that the cryogenic liquid is caused to be drawn through the delivery tube to the dispersive medium due to action caused by a vacuum applied via the exhaust tube from a vacuum source ("negative pressure") located on the exhaust side of the system. Such a "pulling" of the cryogenic liquid from the exhaust side is to be contrasted to previous cryogenic systems wherein the cryogenic liquid is "pushed" from the delivery side (i.e. wherein the cryogenic liquid is forced through the delivery tube to the dispersive medium by a pressure source/pump ("positive pressure") located on the delivery side of the system).

The use of a sintered material as the dispersive medium advantageously enable a control and/or configuration of the material's porosity properties. The porous nature of sintered material and its use in examples of the present invention enables the cryogenic gas to freely pass through and egress from the dispersive medium. This enables a negative pressure from the vacuum source to be communicated through: the exhaust line, the dispersive medium and the delivery line to the cryogenic liquid source, i.e. the vacuum source can be in fluid communication with the source of the cryogenic liquid. The vacuum's negative pressure, duly communicated to the cryogenic liquid, provides a lifting effect/pulling or 'sucking' of the cryogenic liquid towards the probe tip and to the dispersive medium therein.

As a result of the thermal transfer that occurs between the cryogenic liquid, dispersive medium and probe tip during use, an ice ball 221 can form around the probe tip 205. When the probe tip is inserted into tissue required for destruction an ice ball within the surrounding tissue is formed reducing the tissue in the ice ball below its survival temperature (−20° C.).

The centre of the ice ball 214' is typically as cold as the thermal source generating the ice ball. Where, for example, liquid Nitrogen is used as the cryogenic liquid, tissue immediately adjacent to the probe tip will be reduced to −196° C. or thereabouts. The margins of the ice ball 221' will be at 0° C. Between these two points 214' 221' there is a thermocline and depending on how long and how quick the freeze takes place will determine how much of the ice formed is effectively lethal to the frozen tissue.

The above cryogenic systems and their methods of use provide:
Improved freeze rates
Reduced losses
Shorter freeze times, particularly, the probe may begin to cool in less than 2 minutes
Reduced variation of pressure/flow on cryoprobe performance
Increased safety
The capacity to allow for multiuse of probes and other components Each of the probes describe above may be used with the system set out in FIG. 9, providing appropriate couplings are provided.

Figure 11A:
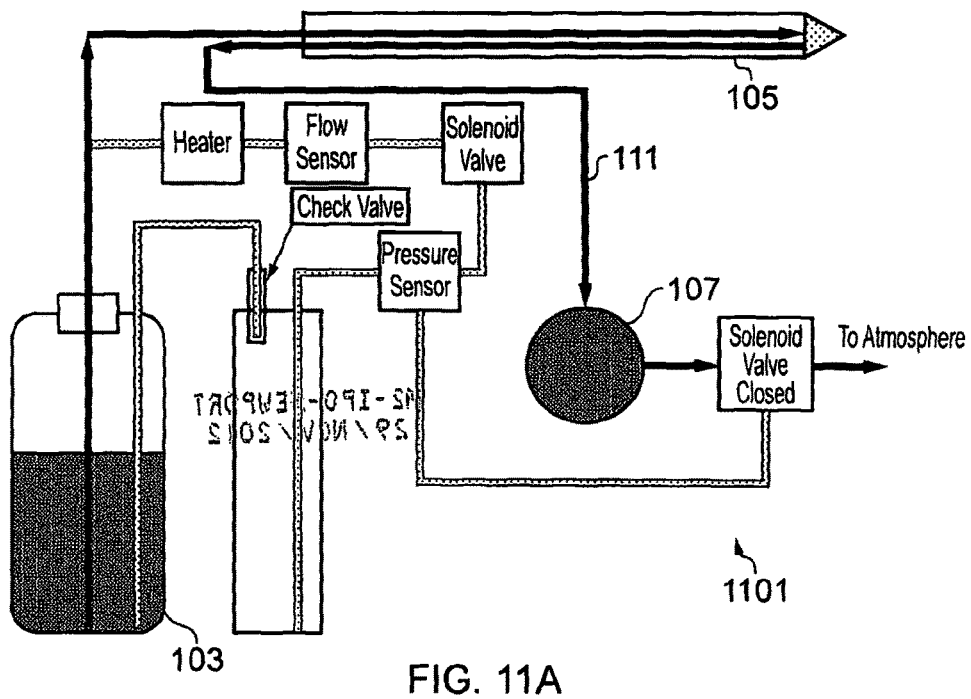
FIG. 11A is a schematic view of a freezing mode of operation of an example of the present invention.

FIG. 11A illustrates a flow path of cryogen through an apparatus for cryosurgery 1101 during a freeze mode of operation. In the freeze mode, liquid cryogen is drawn from storage Dewar 103 to the tip of probe 105 via vacuum pump 107. The liquid cryogen evaporates in the sintered material of the probe tip. The gaseous cryogen is exhausted from the probe via the vacuum pump 107 and vented out to atmosphere.

Figure 11B:
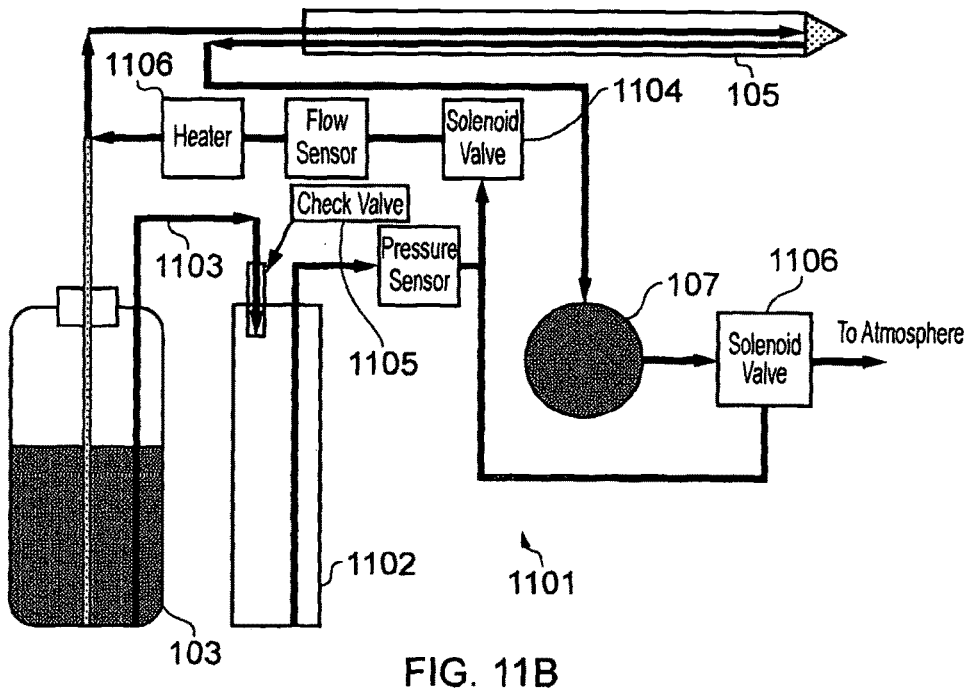
FIG. 11B is a schematic view of thawing mode of operation of the example of FIG. 11A.

FIG. 11B shows the apparatus 1101 during a thaw mode of operation, for example after a freezing mode had taken place.

The apparatus for cryosurgery 1101 comprises a flash chamber 1102. This is a pressure vessel manufactured from thick walled aluminium tube sealed at both ends and fitted with two metric threaded ports. A pipe 1103 submerged in the liquid nitrogen of the cryogen source 103 is connected to one of the ports on the flash chamber. The second port is connected to the vacuum pump 107 via a valve 1104. There is a check valve 1105 positioned between the connection to the flash chamber and the pipe submerged in the liquid nitrogen.

When the valve 1104 opens suction is applied to the flash chamber. Once the air is evacuated, the check valve 1105 opens and a small quantity of liquid nitrogen is drawn from the Dewar into the flash chamber. When the liquid arrives in the flash chamber it immediately evaporates when it contacts the heated walls of the flash chamber.

Because a volume of liquid nitrogen expands into a volume of nitrogen gas at the ratio of 700 to 1, the flash chamber quickly fills with nitrogen gas under pressure. This pressure forces the check valve to close and the flow of liquid nitrogen into the flash chamber is turned off. The pure nitrogen gas then flows from the flash chamber via the control valve 1104 through a heater/heat exchanger 1106 and to the probe 105 where the heat from the gas is transferred to the probe tip so that thawing of the probe tip may take place. The flash chamber thus acts as a source of gaseous cryogen for delivery to the probe.

The gas from the probe is then re-circulated via the vacuum source/compressor 107 back into the heater/heat exchanger 1106 and again back into the probe 105. This loop continues until the thaw is complete at which time the valve 1104 closes and suction is no longer applied to the flash chamber at which point it remains pressurised until required again.

A valve 1106 in the exhaust line and the vacuum pump 107 allows, during a freezing mode, the spent nitrogen gas generated during a freeze cycle to pass to the atmosphere. The valve also allows, during a thawing mode, nitrogen gas to be re-circulated around the probe and heated before being passed through the probe in a thaw cycle.

Re-using the cryogenic gas in this manner avoids the need to use air/atmospheric gas as the thawing medium. If air/atmospheric gas were to be used, moisture would need to be eliminated from the air using a combination of desiccant filters/compressed air dryers and process heaters to eliminate the moisture. If moisture were to reach the probe tip and subsequently remained there whilst a freeze cycle was in place this would cause a blockage in the probe. Accordingly, reliability of the apparatus is improved since there is no reliance on a user to remember to change the desiccant filter and carry out routine maintenance on a compressed air dryer. Therefore a simpler and more reliable method is provided.

Also, re-using the cryogenic gas in this manner avoids the need to use a separate source of thawing medium. The apparatus 1101 effectively, efficiently and cheaply enables access to the enormous volumes of gaseous cryogen available in liquid form inside the Dewar cryogen source.

It will be appreciated that the invention is not limited to the forgoing description of a preferred example and that modifications may be made within the scope of the Claims appended hereto. Indeed, various modification will be apparent to those skilled in the art, for example, the microprocessor control could be replaced by direct control be a skilled technician. Instead of liquid nitrogen an alternative liquid cryogen may be used. An alternative method of supplying liquid cryogen, e.g. a pump, may be used. The probe tip may be warmed by use of an electric resistance coil instead of hot nitrogen gas. Any controllable vacuum source may be used with the present invention.

The invention claimed is:

1. An apparatus for cryosurgery comprising;
a probe comprising a dispersive medium, a thermally conductive tapered probe tip, and a supply line, wherein the dispersive medium extends about and outwardly from the supply line to the thermally conductive tapered probe tip, and is in thermal communication with the thermally conductive tapered probe tip about the supply line, so as to generate, in use, an ice ball about the periphery of the thermally conductive tapered probe tip, the supply line extending into the thermally conductive tapered probe tip;
an exhaust line configured to receive cryogen from the probe; and
a vacuum source configured to be in fluid communication with the exhaust line, and wherein the apparatus is configured such that, in use, cryogen is drawn from a cryogen source for delivery to the probe by the vacuum source.

2. The apparatus according to claim 1, wherein the vacuum source is configured to continuously evacuate the exhaust line.

3. The apparatus according to claim 1, wherein the cryogen source comprises a source of liquid cryogen.

4. The apparatus according to claim 1, wherein the apparatus is configured such that the cryogen received from the probe via the exhaust line is re-circulated for re-delivery to the probe.

5. The apparatus according to claim 1, wherein said dispersive medium is configured such that, in use, cryogen delivered to the probe disperses through the dispersive medium.

6. The apparatus according to claim 5, further comprising a delivery line configured to deliver cryogen to the probe, wherein the dispersive medium is configured so as to enable fluid communication between the delivery line and the vacuum source.

7. The apparatus according to claim 5, wherein the dispersive medium comprises at least one of: a porous material, a sintered material, a sintered metal, ceramic or plastic.

8. The apparatus according to claim 1, wherein the vacuum source is downstream of the exhaust line.

9. The apparatus according to claim 1, further comprising a vacuum reservoir, provided upstream of the vacuum source.

10. The apparatus according to claim 9, wherein the vacuum reservoir is in communication with a heat exchanger, heating element or other cryogen heating means.

11. The apparatus according to claim 1, wherein the exhaust line comprises peripheral insulation.

12. The apparatus according to claim 11, wherein the peripheral insulation is provided, at least in part, by a vacuum jacket.

13. The apparatus according to claim 12, wherein the vacuum jacket is in fluid communication with the vacuum source.

14. The apparatus according to claim 12, wherein the vacuum jacket is in fluid communication with the exhaust line.

15. The apparatus according to claim 12, wherein the vacuum jacket comprises a one way value.

16. The apparatus according to claim 1, further comprising a delivery line configured to deliver liquid cryogen to the probe, wherein for at least part of its length the delivery line extends along at least part of the exhaust line.

17. The apparatus according to claim 1, wherein the vacuum source comprises a pump.

18. A probe for cryosurgery comprising:
a thermally conductive tapered probe tip;
a supply line;
an exhaust tube located concentrically about the supply line, and
a dispersive medium provided within said thermally conductive tapered probe tip, the dispersive medium extends about and outwardly from the supply line to the thermally conductive tapered probe tip and is in thermal communication with the thermally conductive tapered probe tip about the supply line, configured such that, in use, cryogen delivered to the probe disperses within the probe through the dispersive medium, so as to generate, in use, an ice ball about the periphery of the thermally conductive tapered probe tip.

19. The probe according to claim 18, wherein the dispersive medium is configured so as to enable fluid communication between a delivery line configured to deliver cryogen to the probe and an exhaust line configured to receive cryogen from the probe.

20. A probe for cryosurgery, the probe comprising:
a distal end and a proximal end;
a tapered, thermally conducting and rigid probe tip at the distal end;
a dispersive medium thermally coupled to the tapered, thermally conducting and rigid probe tip;

a cryogen inlet tube having an end which extends into the tapered, thermally conducting and rigid probe tip, the cryogen inlet tube being received within the dispersive medium such that, in use, cryogen delivered to the probe disperses within the probe from the end of the cryogen inlet tube and through the dispersive medium;

a cryogen outlet tube in fluid communication with the cryogen inlet tube via the dispersive medium;

the cryogen outlet tube being provided concentrically about the cryogen inlet tube, the tapered, thermally conducting and rigid probe tip being insertable into tissue to effect cryosurgery thereon.

21. A probe for cryosurgery, for example liquid cryosurgery, the probe comprising a proximal end for connection to a cryogen delivery line and a tapered, rigid and thermally conductive distal end for locating within tissue for effecting cryosurgery thereon, a dispersive medium being located at the distal end of the probe, the probe comprising a cryogen supply line extending into the tapered, rigid and thermally conductive distal end and a cryogen exhaust line, the exhaust line being provided concentrically about the supply line and along the entire length thereof, the supply line protruding into the dispersive medium through which cryogen fluidly communicates between the cryogen supply line and cryogen exhaust line.

* * * * *